United States Patent [19]

Heyman

[11] 4,062,227
[45] Dec. 13, 1977

[54] CW ULTRASONIC BOLT TENSIONING MONITOR

[75] Inventor: Joseph S. Heyman, Gloucester, Va.

[73] Assignee: The United States of America as represented by the Administrator of the National Aeronautics and Space Administration, Washington, D.C.

[21] Appl. No.: 754,066

[22] Filed: Dec. 23, 1976

[51] Int. Cl.² ............................................. G01N 29/00
[52] U.S. Cl. ........................................ 73/630; 73/579; 73/88 F
[58] Field of Search ...................... 73/61 R, 67.6, 67.7, 73/67.8 R, 88 F, 560, 67.2, 24, 32 A

[56] References Cited

U.S. PATENT DOCUMENTS

| 3,306,100 | 2/1967 | Wilhelm et al. | 73/67.2 |
| 4,015,464 | 4/1977 | Miller et al. | 73/61 |

FOREIGN PATENT DOCUMENTS

| 2,321,606 | 11/1974 | Germany | 73/560 |

*Primary Examiner*—Richard C. Queisser
*Assistant Examiner*—John P. Beauchamp

*Attorney, Agent, or Firm*—Howard J. Osborn; William H. King; John R. Manning

[57] ABSTRACT

This invention is a CW ultrasonic device for measuring frequency shifts of the peak of a mechanical resonance in a body. One application of the device is measuring the strain in a bolt. It also has other applications such, for example, as measuring the thickness of a body, measuring the depth of a flaw in a body, measuring the elongation of body and measuring changes in velocity of sound in a body. The body is connected, by means of a CW transducer, to electrical circuit means including a narrow band RF amplifier to form a closed loop feedback marginal oscillator that frequency locks the device to the peak of a mechanical resonance in the body. Thereafter, when the frequency of this peak changes, because of a physical change in the body, the frequency of the oscillator changes. The device includes an automatic frequency resonant peak tracker that produces a voltage that is related to a change in frequency of the oscillator. This voltage is applied to the RF amplifier to change the center of its frequency band to include the frequency of the peak and is a measure of the frequency shift. The device also includes a special transducer which requires contact to only one side of the body and provides high electrical isolation between its parts.

9 Claims, 10 Drawing Figures

CW ULTRASONIC BOLT TENSIONING MONITOR

ORIGIN OF THE INVENTION

The invention described herein was made by an employee of the U.S. Government and may be manufactured and used by the Government for governmental purposes without the payment of any royalties thereon or therefor.

BACKGROUND OF THE INVENTION

The invention relates generally to a continuous wave (CW) device for measuring frequency shifts in the peak of a mechanical resonance in a body due to changes in the physical characteristics of the body and more specifically concerns a CW ultrasonic device for measuring strain in a bolt.

Although there are many methods available for measuring strain in bolts, the torque wrench is the general accepted technique and justly so-for most applications. However, for critical assemblies, the accuracy of a torque wrench may lead to improperly stressed bolts due to friction between the threads as well as between the nut and the work. The "calibration" of torque wrenches assumes that 40 percent of the usable applied force is dissipated in friction but in fact, this number varies greatly with configuration, roughness, lubrication, etc. Because of the calibration uncertainty, components bolted with torque wrenches must be overdesigned leading to increased cost and weight or must suffer a reduced reliability. An excellent method for measuring bolt strain is the strain gage bolt, which uses a standard resistance strain gage mounted to the body of the bolt. This approach results in a highly accurate bolt strain monitor at a cost of several hundreds of dollars per bolt but measures only the local strain under the gage. Another technique used if both sides of the bolt are accessible, is a simple caliper to directly measure bolt elongation. However, in many instances this is not possible and a more sophisticated approach is required.

An ultrasonic technique using pulse echo is available which can resolve stress produced steel bolt elongation for one echo on the order of $\pm 10^{-2}$ mm. Although this is excellent length resolution, a 0.1 percent elongation of a 100-mm bolt, based on this resolution corresponds to a potential strain accuracy of only $\pm 10$ percent with less strain having correspondingly poorer accuracy. In addition, pulse-echo systems must utilize fast risetime pulses to achieve such accuracy which adds to the cost and complexity of the technique. Although this resolution may be improved with higher echo numbers, this places a constraint on bolt parallelism.

It is therefore the primary object of this invention to provide a CW ultrasonic device for measuring the strain in a bolt that is simple in operation, that has high accuracy and that has a potential low cost.

Another object of this invention is to provide a CW ultrasonic device for measuring frequency shifts in the peak of a mechanical resonance of a body due to changes in the physical or electrical characteristics of the body.

A further object of this invention is to provide an improved reflection type CW ultrasonic transducer.

Other objects and advantages of this invention will become apparent in the following specification and drawings.

SUMMARY OF THE INVENTION

The invention is a CW ultrasonic device for measuring the change in stress in a bolt. Even though the invention is described as a device for measuring the stress in a bolt, it has many other applications. It can be used to measure the shifts in the frequency of the peak of a mechanical resonance in a solid, liquid, or gas body due to changes in the physical characteristics of the body.

A transducer assembly including a transmitter and a receiver is coupled to a bolt such that CW RF electrical signals applied to the transmitter are converted to sound waves that propagate as a plane wave into the bolt. The reflected sound waves set up standing waves in the bolt and are converted to RF electrical signals by the receiver. The RF signals at the receiver are amplified by a narrow band RF amplifier and then applied to the transmitter. The amplifier includes an automatic gain control feedback circuit that causes the circuit to oscillate at a frequency corresponding to a mechanical resonance peak in the bolt. When the bolt is stressed, the frequency of oscillation changes. An automatic frequency resonant peak tracker is provided to prevent harmonic hopping and to produce a control voltage for changing the frequency response of the amplifier such that it follows the change in the frequency of oscillation. This control voltage is measured to give an indication of the change in stress in the bolt.

DETAILED DESCRIPTION OF THE INVENTION

The embodiment of the invention selected for illustration in the drawings is a Reflection Oscillator Ultrasonic Spectrometer (ROUS) based on continuous wave (CW) techniques which is able to measure changes in stress in a bolt from one end of the bolt.

A simple one-dimentional isolated resonator model applies to ultrasonic waves propagating in the bolt. If the assumption is made that complete reflection occurs at the flat and parallel ends of the bolt; then to a good approximation the resonant frequencies of the bolt are:

$$F_j = \frac{jv}{a} \quad (1)$$

where $j$ is the harmonic integer, $v$ is the velocity of sound and $a/2$ is the length of the bolt. Here, the effect of the transducer on the composite resonator (bolt plus transducer) is neglected since it would enter only as a higher order correction factor in a frequency shift. If the bolt is uniaxially elastically strained, the resonant frequency will shift due to both bolt elongation and a change in the velocity of sound. From equation (1), the change in frequency is seen to be $$\Delta F_j = \frac{jv}{a}\left(\frac{dv}{vda} - \frac{1}{a}\right)\Delta a = F_j\left[\frac{dv}{vda} - \frac{1}{a}\right]\Delta a \quad (2)$$

or relating the frequency to the applied stress with $dv/da = (dv/dS)(dS/da)$:

$$\Delta F_j = F_s\left[\frac{1}{v}\frac{dv}{dS} - \frac{1}{E}\right]\Delta S \quad (3)$$

where $E$ is Youngs modulus and $S$ is the applied stress. The term $v$ depends on the material under tension and for isotropic materials varies linearly with stress determined in part by the third order elastic constants. It is interesting to note that the $dv/dS$ term accounts for about ⅔ of the frequency shift in the steel bolts that were tested. The actual magnitude of this term can be shown to be:

$$\frac{dv}{dS} = \frac{-1}{6\rho(\lambda + 2\mu/3)v}\left[2l + \lambda + \frac{\lambda + \mu}{\mu}(4m + 4\lambda + 10\mu)\right] \quad (4)$$

where $\rho$ is the density at zero strain, $\lambda$ and $\mu$ are the Lamé constants, and $l$, $m$ and $n$ are the higher order elastic constants. Using modern values in (4) with $S$ expressed in Pascal, equation (3) becomes $$\Delta F = F_j(1.8 \times 10^{-11})\,\Delta S\ (Pa)$$

or for 5 MHz ultrasound: $\Delta F = 9.2 \times 10^{-5}\,\Delta S\ (Pa)$ which corresponds to a 1 hertz shift for a $1.1 \times 10^4$ Pa (1 hertz for a 1.6 pound/in.²) load. An ultrasonic system able to resolve 1 hertz shifts can then theoretically resolve 0.1 microstrain.

The ROUS instrument is a closed loop marginal oscillator with gain and frequency feedback control having similar operating characteristics to the TOUS system disclosed in U.S. patent application, Ser. No. 551,913 filed on Feb. 21, 1975 now U.S. Pat. No. 4,015,464. As a closed loop marginal oscillator, the ROUS can be adjusted to measure both changes in loop loss (or "Q") as well as resonant frequency. When acoustically coupled to a bolt, the system can be considered a "bolt stabilized oscillator" (in contrast to a crystal stabilized oscillator) and is sensitive to any parameter changes, in particular stress-produced elongation and change in velocity of sound.

Figure 1:
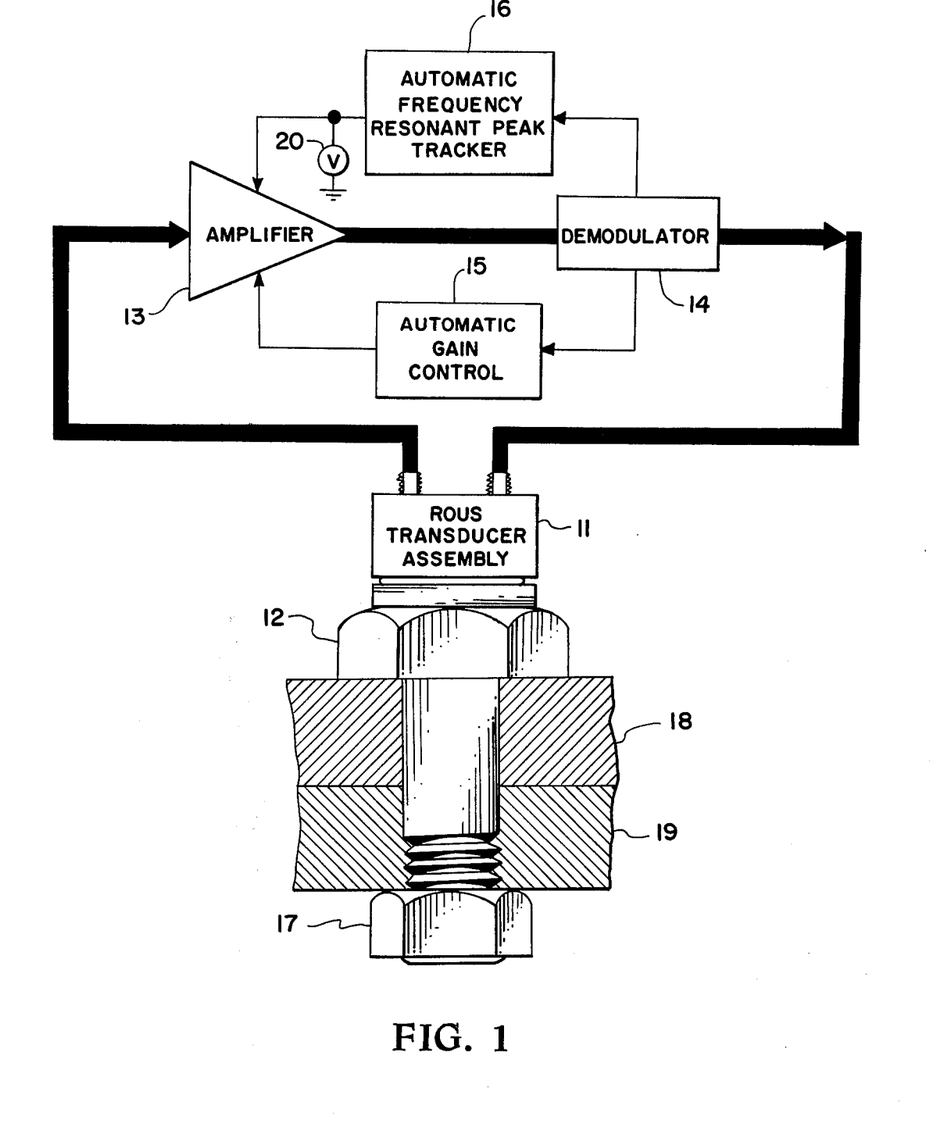
FIG. 1 is a block diagram of the embodiment of the invention selected for illustration.

Turning now to the embodiment of the invention selected for illustration in the drawings, the number 11 in FIG. 1 designates a ROUS transducer assembly which is attached to a bolt 12 whose change in stress is to be measured. Transducer 11 includes a transmitter means which change RF signals into sound waves and receiver means which change the standing sound waves into RF signals. The transducer assembly 11 is disclosed in detail in FIGS. 3, 4 and 5.

The heavy solid lines in FIG. 1 indicate RF signals while the thin lines indicate lower frequency and d.c. signals. The RF signal at the receiver means of transducer assembly 11 is applied to a narrow band RF amplifier 13 the output of which is applied through a demodulator 14 to the transmitter means of transducer assembly 11. The demodulated signal at the output of demodulator 14 is applied to an automatic gain control 15 and an automatic frequency resonant peak tracker 16. The demodulator 14 in addition to providing the demodulated signal also provides isolation between the RF signal at the output of amplifier 13 and the RF signal at the transmitter means of transducer assembly 11.

Automatic gain control 15 includes an amplifier and a low pass filter the output of which controls the gain of amplifier 13. The gain of amplifier 13 is made sufficient by the automatic gain control 15 to just overcome all losses, both electrical and acoustical, and the phase shift around the RF loop in FIG. 1 is made to be some multiple of 2 $\pi$. Hence, the loop will oscillate at a frequency corresponding to a mechanical resonance peak for bolt 12 as indicated in equation (1).

Figure 2:
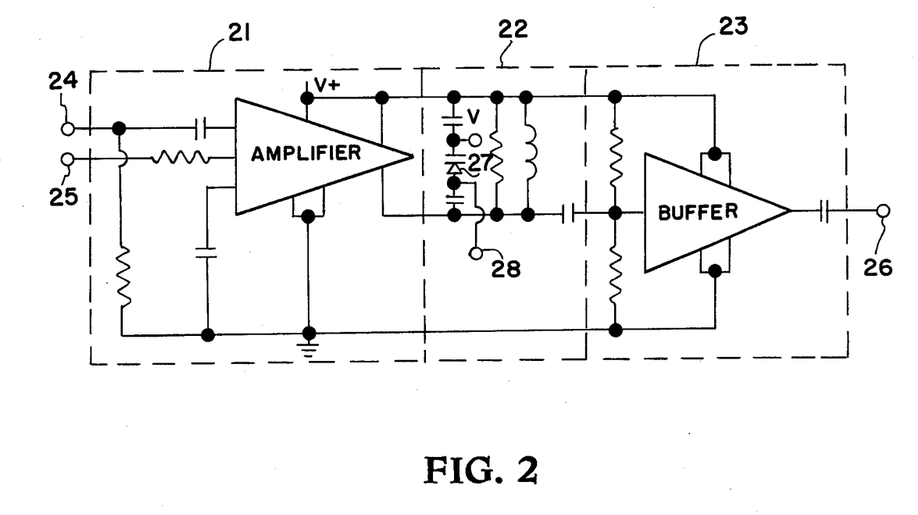
FIG. 2 is a diagram of the narrow band RF amplifier used.

Amplifier 13 which is shown in FIG. 2, consists of an amplifier stage 21, a band pass filter stage 22 and a buffer stage 23. The RF signal from the receiver in transducer assembly 11 is applied to terminal 24, the automatic gain control signal is applied to terminal 25 and the output of the amplifier appears at terminal 26. A varacter diode 27, contained in the band pass filter stage, is controlled by the control voltage from automatic frequency resonant peak tracker 16 which is applied to terminal 28. The control voltage applied to varacter diode 27 changes the capacitance of diode 27 such that the band pass includes the frequency of oscillation.

Figure 3:
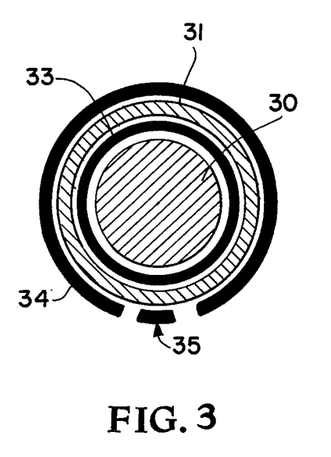
FIG. 3 is a back view of the transducer used by the illustrated embodiment of the invention.
Figures 4, 7:
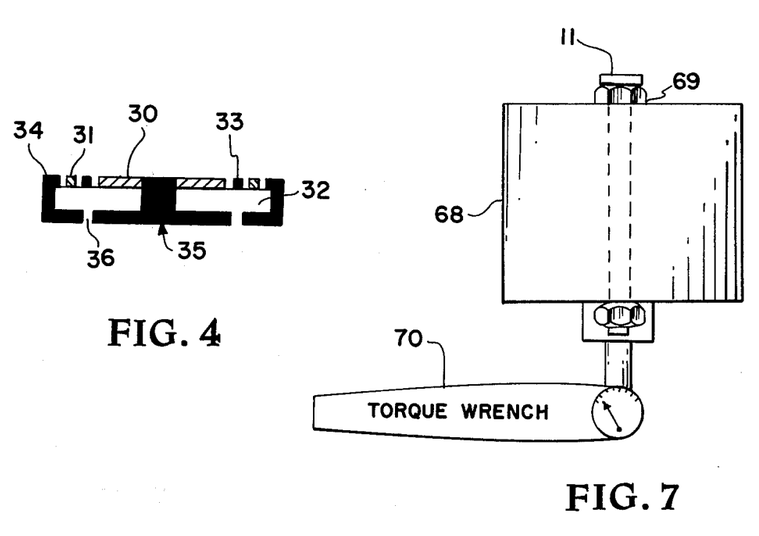
FIG. 4 is a side view of the transducer.
FIG. 7 is a schematic drawing of the apparatus used to test the invention.
Figure 5:
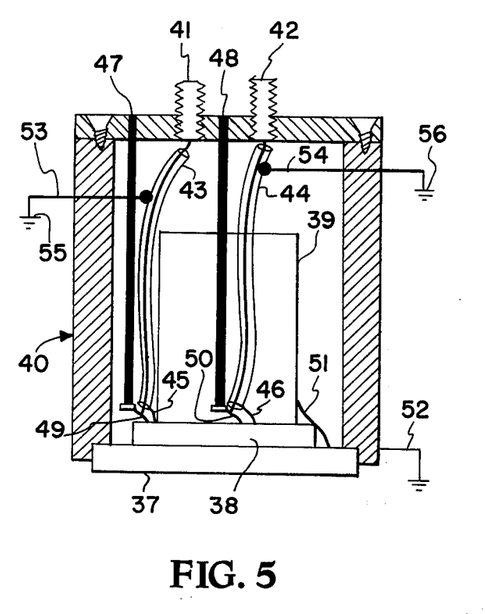
FIG. 5 is a schematic drawing of the transducer assembly.

Back and side views of the transducer used in the embodiment of the invention selected for illustration are shown in FIGS. 3 and 4, respectively. The main purpose of the transducer is to transmit and receive CW ultrasonic waves simultaneously at nearly the same location. Concentric electrodes 30 and 31 are applied to piezoelectric material 32. Either electrode can be the transmitting electrode with the other electrode being the receiving electrode. A ground ring 33 is located between electrodes 30 and 31 to provide isolation between the two electrodes. Two ground planes 34 and 35 are attached to piezoelectric material 32 so that they are separated by a gap 36. These two ground planes provide a separate ground for each electrode and hence greatly improve the isolation between the transmitter and receiver.

The ROUS transducer assembly 11 is shown in FIG. 4. A protective wear plate 37 is bonded to the transducer 38 and a ground plane cylinder 39 is bonded to ground ring 33 on the transducer to improve electrical isolation. An outer shell 40 which holds the assembly together is bonded to protective wear plate 37. Shell 40 has two connectors 41 and 42, that extend through the shell and that are insulated therefrom. A shielded wire 43 connects connector 41 to transducer electrode 31 and a shielded wire 44 connects connector 42 to transducer electrode 30. The shields for wires 43 and 44 are connected to ground planes 34 and 35, respectively, in the transducer by means of wires 45 and 46. Insulating rod contact supports 47 and 48 hold spring contacts 49 and 50 which make contact with electrodes 31 and 30, respectively. A shielded cable 51 connects ground plane cylinder 39 to outer shell 40 which is connected to a ground 52. Cables 53 and 54 are connected to the shields of wires 43 and 44, and extend through the wall of outer shell 40 at any convenient location to separate grounds 55 and 56, respectively. Separate grounds 55 and 56 greatly improves the isolation between electrodes 30 and 31. Having the third ground 52 for ground plane cylinder 39 further improves the isolation between the two electrodes.

Figure 6:
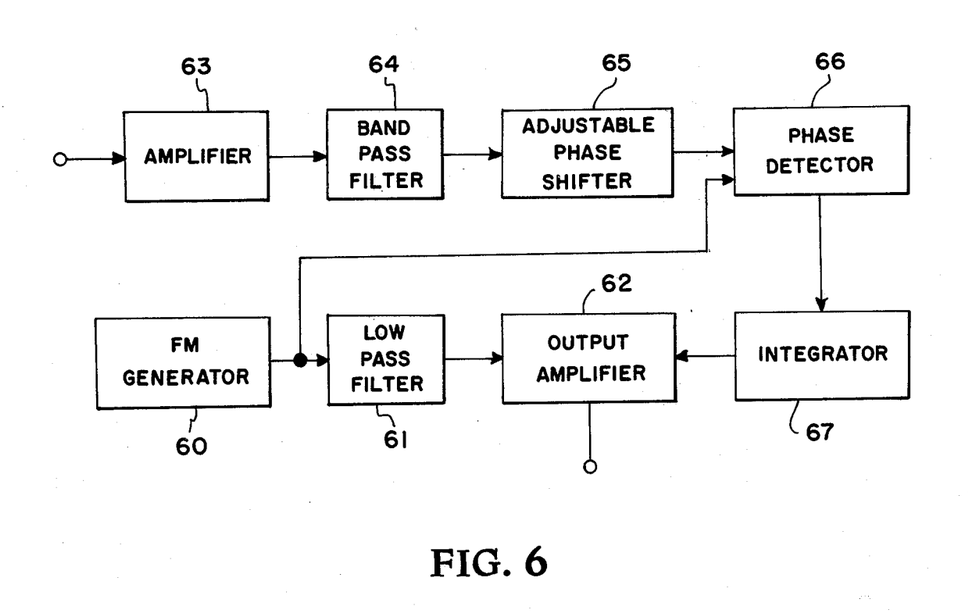
FIG. 6 is a block diagram of the automatic frequency resonant peak tracker.

A block diagram of a device suitable for use as automatic frequency resonant peak tracker 16 is shown in FIG. 6. An FM generator 60 generates square waves at a frequency of 1 kilohertz. It is to be understood that other frequencies can be used, in fact, for some applications other frequencies would probably be preferable to 1 kilohertz. The square waves are applied to a low pass filter 61 which converts them to sine waves. The sine waves are amplified by an output amplifier 62 and then applied to RF amplifier 13. Consequently, this 1 kilohertz signal is mixed with the RF signal at the output of RF amplifier 13. This 1 kilohertz signal is detected by demodulator 14 and then applied to an amplifier 63. The resulting amplified signal is applied through a band pass filter 64 and an adjustable phase shifter 65 to a phase detector 66. The signal at the output of FM generator 60 is also applied to phase detector 66. If the two signals to detector 66 are in phase no output is produced. However, if the two signals are out of phase, detector 66 will produce an output the polarity of which produces a correction in the direction of phase equality. The output of phase detector 66 is integrated by an integrator 67 and then added to the sine wave in output amplifier 62.

In the operation of automatic frequency resonant peak tracker 16, with no strain on bolt 12 phase shifter 65 is adjusted to give a no voltage output of phase detector 66. That is, phase shifter 65 is adjusted to make the output of the phase shifter in phase with the signal generated by FM generator 60. Thereafter, when a strain is applied to bolt 12 the frequency of the resonant peak of the oscillator changes. If the change is such that the band pass of amplifier 13 is in a frequency range below the peak frequency of the oscillator a first phased output of the 1 kilohertz signal is produced at the output of demodulator 14, or if the change is such that the band pass of amplifier 13 is in a frequency range above the peak frequency a second phased output, of the 1 kilohertz, 180° out of phase with the first phased output, is produced at the output of demodulator 14. The reason for the 180° difference in phase is that when operating below the peak frequency a positive frequency shift results in a positive amplitude shift and a negative frequency shift results in a negative amplitude shift. Conversely, when operating above the peak frequency a positive frequency shift results in a negative amplitude shift and a negative frequency shift results in a positive amplitude shift. Consequently, whenever the frequency of the resonant peak of the oscillator changes due to a change in strain in bolt 12 either the first or second phased signal appears at the output of demodulator 14. The phase of this phased signal is compared with the phase of the signal produced by FM generator 60 in phase detector 66. Since there is a difference in phase, a voltage is produced at the output of phase detector 66. This voltage is applied to amplifier 13 to change its frequency range to include the frequency of the resonant peak. This voltage applied to amplifier 13 is measured by a voltmeter 20 to give an indication of the strain in bolt 12.

When the ROUS transducer assembly 11 is mounted to bolt 12 via a thin layer of coupling agent between the bolt and contact plate 30 the system will oscillate at a frequency corresponding to a harmonic of the bolt satisfying equation (1). By choosing a sufficiently high harmonic, the effective mode of propagation is plane wave so the acoustic beam does not appreciably spread. The frequency separation between harmonics is $\Delta F = v/a$ which for a 10-cm steel bolt is about 25 KHz. For the system to resolve individual harmonics, the mechanical resonance $\frac{1}{2}$ width must be less than 25 KHz with system accuracy increasing with decreasing $\frac{1}{2}$ width. Typically, one mechanical resonance near the desired harmonic is much stronger than others and is the best operating frequency.

The automatic frequency resonant tracker 16 and voltmeter 20 are used to function primarily as a frequency shift monitor. The fundamental locking scheme FM's the center frequency of the RF amplifier 13, (3 dB bandwith at 100 KHz) at a kilohertz rate and phase detects the resulting kilohertz amplitude modulated RF envelope. At the peak of the mechanical resonance, a sharp null occurs in the 1 kilohertz detected signal. The detected signal also generates an off null control voltage to center the frequency of the RF amplifier. Therefore, the amplifier center frequency tracks the peak of the mechanical resonance and the control voltage as measured by voltmeter 20 is used to monitor the resonance frequency shift. This results in a rather simple frequency readout. An additional desirable function of the RF amplifier 13 bandpass prevents the ROUS from hopping to a different harmonic of equal Q which, although unlikely may occur without the bandpass for a long bolt having several harmonic peaks of nearly equal amplitude.

As an evaluation of the ROUS bolt monitor simultaneous data was obtained of bolt stress, frequency shift, and torque applied for the test configuration shown in FIG. 7. The apparatus consists of a $10^5$ Newton strain gage load cell 68, a mild steel bolt 69, 1.27cm by 7.87 threads per cm, 8.89 cm long ($\frac{1}{2}$ inch by 20 threads per inch, 3½ inches long) with ends ground fat and parallel to 1/5 acoustic wavelength and a high quality gage torque wrench 70. The ROUS transducer assembly 11 is acoustically coupled to the bolt with a dab of dehydrated stop cock grease (heated NONAQ) and carefully "rung in" to make an acoustic bond. This entails moving the transducer in a random fashion until a thin layer of grease coats the head of the bolt. A small mechanical clip magnetic clamp or vacuum clamp is adequate to maintain constant coupling between the bolt and transducer during tightening of the bolt.

Figure 8:
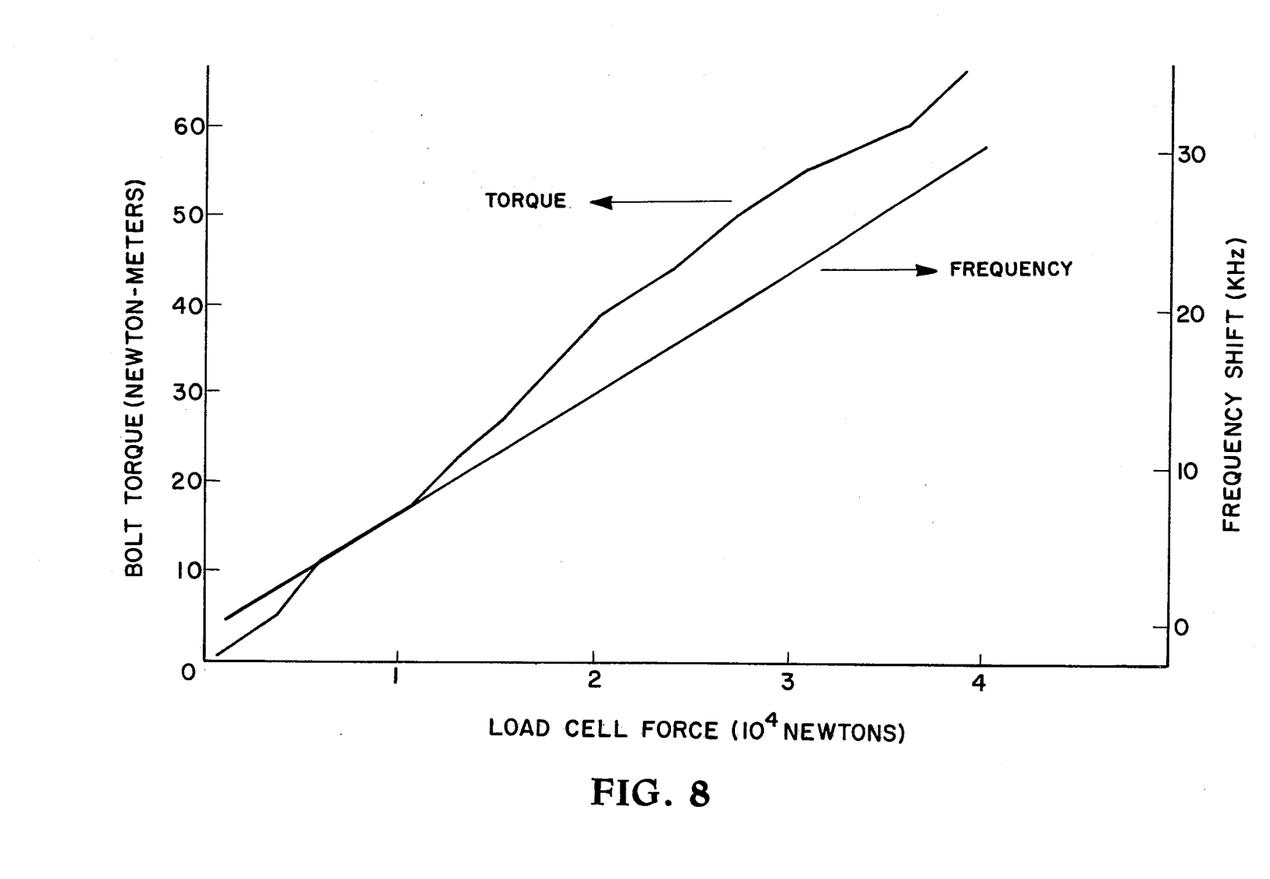
FIG. 8 is a graph of test results of the invention demonstrating its linearity for low stresses.

FIG. 8 is a typical result demonstrating the linearity of the monitor for low stresses. A slight departure from linearity above $3 \times 10^4$ Newton ($33 \times 10^3$ psi) is apparent and indicative of the transition to plastic deformation of the bolt. The corresponding figure for torque is not a straight line and cannot be accurately calibrated for stress due to an unknown and variable coefficient of friction. This is further illustrated in FIG. 9 which represents 20 cycles of "torquing" a dry bolt to 67 Newton-meters. The increase in bolt friction reduces the applied stress for cycle 20 to 30% of that for cycle 1. The ROUS monitor (shown by the solid curves) reproduce the same curve fairly well considering the heating effects generated by the dry bolt friction. In this case, a torque instrument (data shown by the dashed lines) is unsuitable for determining the true stress in the bolt and if used would lead to significant configuration error.

Figure 9:
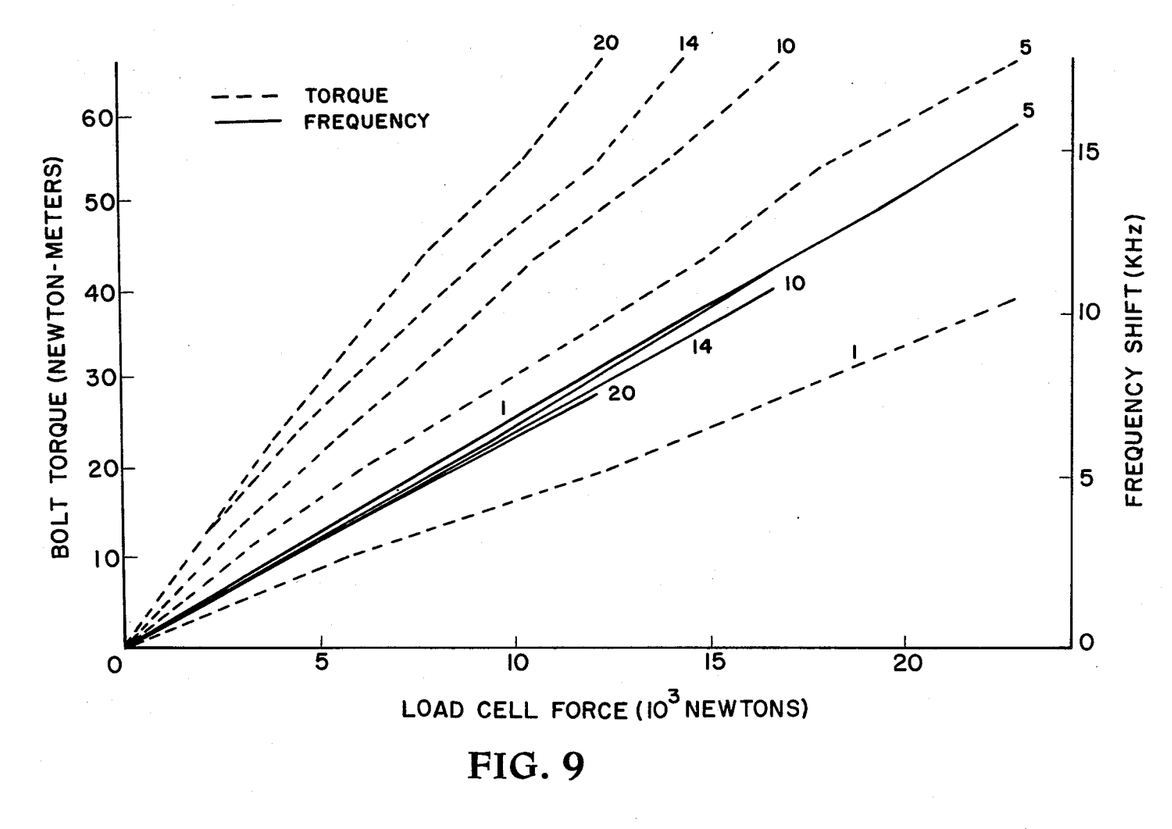
FIG. 9 is a graph demonstrating that the present invention is much more accurate than a torque wrench in measuring stresses.

The slight change in slope of the ROUS curve shown in FIG. 9 from cycle 1 to cycle 10 was observed for all the mild steel bolts tested. Since the zero stress resonance measurements did not vary, the slope variation cannot be attributed to a permanent elongation of the tested bolt. In fact, the slope variation appears to be due to a slight "flow" of the nut and bolt threads thereby distributing the stress differently in cycle 1 than in cycle 10. Once the "flow" equilibrium has occurred, very slight cyclic slope variation occurs as evidenced by cycle 14 and 20 data.

Figure 10:
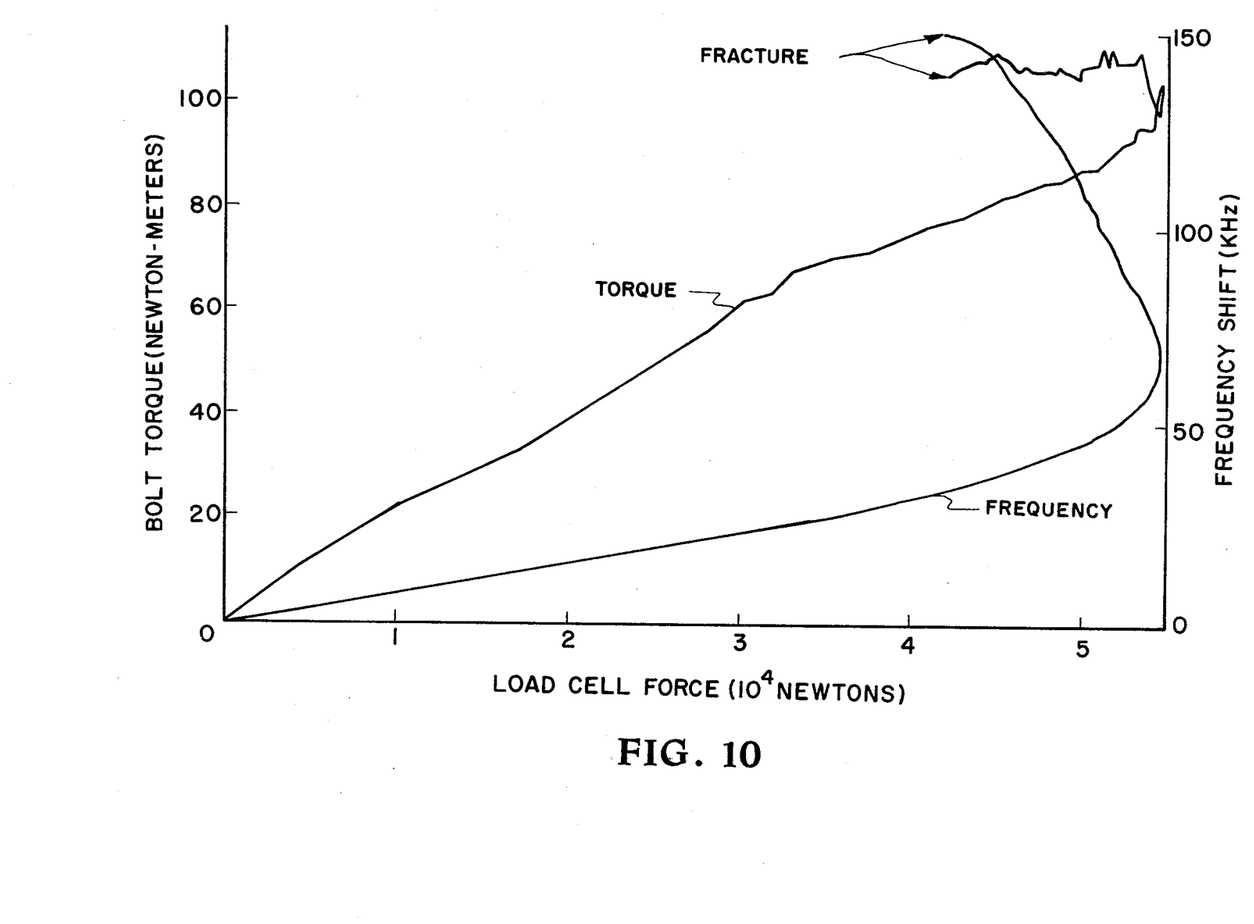
FIG. 10 is a graph further demonstrating the advantages of the present invention over a torque wrench.

A further demonstration of the capability of the ROUS is shown in FIG. 10. This data represents a test in which a bolt was stressed from the elastic region (linear part of the curve) to the plastic region (nonlinear range) to fracture failure. The torque curve illustrates that until plastic deformation occurs, there is little if any warning of the impending bolt failure. For example, in FIG. 8, a torque of 111 Newton-meters for curve 20 would result in a load of $5 \times 10^3$ pounds ($16 \times 10^2$ Mpa), well under the plastic region while 111 Newton-meters for curve 1 would result in a load of $15 \times 10^3$ pounds ($54 \times 10^2$ Mpa) which is beyond the strength of the bolt. The frequency shift curve, however, can be considered an absolute stress measurement so that over stress (or under stress) would be improbable.

One concern over the use of the instrument is the amount of bolt preparation necessary to use the ROUS. FIG. 10 is a pulse echo decay of a tested bolt which had a SCW half-power width of 4 KHz. Although this bolt is not perfectly flat and parallel, it has an adequate geometry for the ROUS monitor so that the additional expense for prepared bolts is nominal.

A further use of this instrument is possible if specially prepared bolts are available. If the bolts used are ground to a specific length, then periodic monitoring of bolt stress is possible if the temperature is known. As an example, a 4 cm long bolt will shift resonance frequency by about 400 Hz/°K due to thermal expansion and sound velocity changes. It is necessary, therefore, to measure the ambient temperature when tightening the bolt or use a comparison standard if periodic monitoring is desirable. In addition, the transducer should be applied to the bolt with considerable care since variations in bond thickness also cause readout error for periodic monitoring. In repeated laboratory bonding of a transducer to a bolt, the change in resonance frequency due to bond thickness variation could be held to less than 200 Hz. Even though there will be a loss in accuracy, it appears that periodic monitoring of stress is possible with this technique.

Even though this invention has been described as a bolt strain monitor, it is obvious that it can have many other applications. For example, it can be used to monitor strain in any body, it can be used to measure changes in length or velocity of sound in a body, it can be used to locate flaws in a body and it can be used to measure the thickness of a body. The invention can be used to monitor the changes of any physical characteristics of a body that results in changes of the frequency of the peak of a mechanical resonance of the body. Also the frequency of oscillation can be measured directly with a frequency counter instead of with voltmeter 20 as disclosed.

What is claimed is:

1. A CW ultrasonic device for monitoring frequency shifts of the peak frequency of a mechanical resonance of a body comprising:

transducer means including a transmitter means attached to said body for changing electrical signals into sound waves for transmission into said body and including a receiver means attached to said body for receiving sound waves from said body and changing the received sound waves into electrical signals:

electrical circuit means connected between said receiver means and said transmitter means for forming a closed loop marginal oscillator with said body that oscillates at a resonant frequency of said body; and means for measuring any shift in frequency of said oscillator whereby the shift in frequency is indicative of a frequency shift of the peak frequency of a mechanical resonance of said body.

2. A CW ultrasonic device according to claim 1 wherein said transmitter means and said receiver means are adjacent each other such that said receiver means receives sound waves that are transmitted by said transmitter means and reflected by said body.

3. A CW ultrasonic device according to claim 2 wherein said body is a bolt whereby a frequency shift of said oscillator is indicative of the strain in said bolt.

4. A CW ultrasonic device according to claim 1 wherein said means for measuring any shift in frequency of said oscillator includes means for generating a voltage related to the shift in frequency and means for measuring the voltage.

5. A CW ultrasonic device according to claim 1 wherein said electrical circuit means connected between said receiver means and said transmitter means for forming a closed loop marginal oscillator includes a narrow band RF amplifier.

6. A CW ultrasonic device according to claim 5 wherein said means for measuring any shift in frequency of said oscillator includes means connected to the output of said amplifier for producing a voltage indicative of any change in the frequency of said marginal oscillator.

7. A CW ultrasonic device according to claim 6 wherein said RF amplifier includes voltage responsive means for changing the frequency band of said RF amplifier and said means for producing a voltage indicative of any change in the frequency of said marginal oscillator includes an audio frequency generator and means for applying the audio frequency signal generated by said audio frequency generator to said voltage responsive means.

8. A CW ultrasonic device according to claim 6 wherein said means for measuring any shift in frequency of said oscillator includes means receiving said voltage indicative of any change in the frequency of said marginal oscillator for changing the frequency band of said RF amplifier so that it includes the frequency at the resonant peak of said oscillator.

9. A CW ultrasonic device according to claim 7 wherein means are provided at the output of said RF amplifier for detecting the said audio frequency signal; means for comparing the phase of said detected audio frequency signal with the phase of said generated audio frequency signal and for generating a voltage indicative of any difference in phase; and means for adding said difference in phase voltage to said audio frequency signal before it is applied to said voltage responsive means.

* * * * *